United States Patent [19]

Graham et al.

[11] Patent Number: 4,697,697
[45] Date of Patent: Oct. 6, 1987

[54] METHOD AND APPARATUS FOR PACKAGING AN INTRAOCULAR LENS

[75] Inventors: William M. Graham, Burton; Wade C. Vaughn, Seattle; Charles M. Inman, Issaquah, all of Wash.

[73] Assignee: CooperVision, Inc., Palo Alto, Calif.

[21] Appl. No.: 897,313

[22] Filed: Aug. 18, 1986

[51] Int. Cl.⁴ .......................... B65D 81/22; A61F 1/16
[52] U.S. Cl. .................................... 206/5.1; 206/438; 206/205; 623/6
[58] Field of Search ................. 623/4, 6; 206/5.1, 205, 206/570, 438, 210

[56] References Cited

U.S. PATENT DOCUMENTS

| | | | |
|---|---|---|---|
| 4,113,088 | 9/1978 | Binkhorst | 206/210 |
| 4,257,521 | 3/1981 | Poler | 206/5.1 |
| 4,326,306 | 4/1982 | Poler | 206/5.1 X |
| 4,423,809 | 1/1984 | Mazzocco | 206/210 X |
| 4,527,294 | 7/1985 | Heslin | 206/210 X |
| 4,586,930 | 5/1986 | Kelman | 206/438 X |
| 4,615,703 | 10/1986 | Callahan et al. | 206/210 X |

FOREIGN PATENT DOCUMENTS 1246  1/1974  Japan .................................. 206/5.1

OTHER PUBLICATIONS

Brochure (undated) available from CooperVision IOL entitled "NOVAsoft".

Primary Examiner—William Price
Attorney, Agent, or Firm—Vorys, Sater, Seymour and Pease

[57] ABSTRACT

A retainer for retaining an intraocular lens in a sterile liquid in a vial includes an elongated pair of side walls defining a lens-receiving area therebetween. A transversely-extending wall between the side walls defines a support surface for the edges of the haptic of the lens. Ribs on the interior surfaces of the side walls terminate short of the transversely-extending wall to define slots for retaining the haptic of the lens. An access opening is defined by the transversely-extending wall to permit the retained lens to be freed for removal by an instrument from without the confines of the retainer. The retainer terminates in its upper portion in a pair of protruding tabs defining slots for receiving an instrument for removing the retainer and the lens from the vial. The method of inserting and removing the lens from the retainer is also described.

14 Claims, 4 Drawing Figures

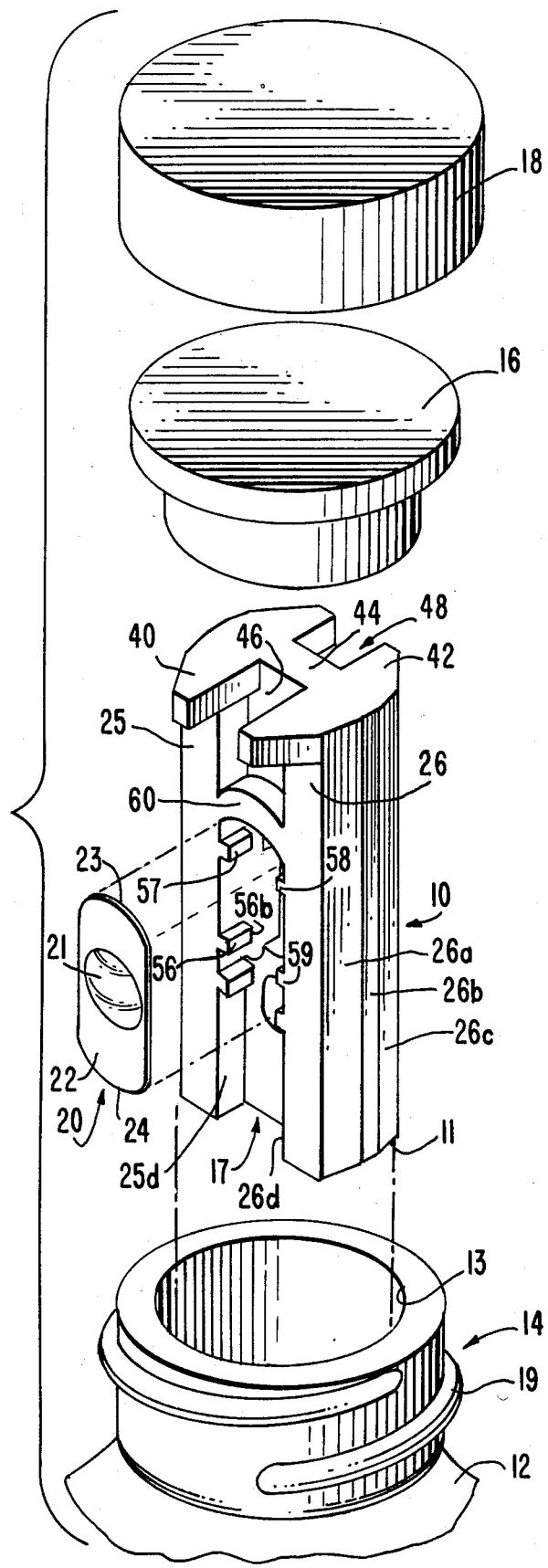

METHOD AND APPARATUS FOR PACKAGING AN INTRAOCULAR LENS

This invention relates to a method and apparatus for packaging an intraocular lens, and in particular a silicone intraocular lens. Still more particularly, this invention relates to a retainer for retaining an intraocular lens while the retainer and lens are inserted into a vial containing sterile fluid. Still more particularly, this invention relates to a retainer for securely retaining an intraocular lens within a vial such that the retainer and the lens may be removed easily from the vial during a surgical procedure and the lens easily accessed and removed from the retainer.

A variety of intraocular lenses including optic elements and supporting haptic structures are known. In order to facilitate the surgical implantation of such lenses it is important that they be safely and securely retained or packaged in a way which permits them to be readily dispensed during surgery. An example of one type of dispenser is found in U.S. Pat. No. 4,257,521 which describes a packaging mount for a lens and haptic assembly in the form of a relatively-stiff, compliant sheet material, such as stainless steel, which is bent and folded to define an integral spring hinge between a longer lower panel and a shorter upper panel. The respective panels are detachably engaged to receive therebetween in a coacting formation an inserted lens and haptic assembly. The lens-loaded mount is resiliently retained against end-shake displacement within a glass-bottle container.

Because such a device is preferably made from stainless steel, clamping of the lens is achieved by forming metal tabs so that the lens is removed from the device by manually bending tabs away from the lens. Such a device is not entirely satisfactory because it is cumbersome, inconvenient to use, and presents a significant risk of tearing surgical gloves on the metallic element(s) when removing the lens from the mount.

Accordingly, it is a general object of this invention to provide a secure method of packaging an intraocular lens, and in particular a silicone intraocular lens.

It is another object of this invention to provide a retainer for insertion in a glass vial partially filled with a sterile liquid wherein the lens is secured to the retainer within the vial so that when a stopper is provided on the vial, the package is ready for safe and secure shipping of the lens to the customer.

It is an additional object of this invention to provide a retainer with clips that retain an intraocular lens, and in particular a silicone intraocular lens, by flexing the edges of the haptic of the lens beneath clips integrally formed with the retainer to retain the lens securely on the retainer.

It is still another object of this invention to provide a retainer for securing an intraocular lens in a vial having protruding tabs at the upper portion thereof with slots therein to receive forceps or other suitable surgical instruments for removal of the retainer from the vial.

It is still an additional object of this invention to provide a retainer which is structurally adapted for receiving the optical portion of an intraocular lens in an oblong slot further structurally adapted to provide a clearance for forceps or other instruments for easy removal of the retainer and attached intraocular lens from the container. Protruding tabs keep the retainer centered in the vial neck and to keep it restricted in movement during shipping.

These and other objects of the invention will become apparent from the written description of the invention which follows.

BRIEF SUMMARY OF THE INVENTION

Directed to achieving the foregoing objects of the invention and overcoming the problems associated with known intraocular lens packaging, a retainer according to the invention is structurally adapted for insertion into a vial containing a sterile liquid. The retainer includes a length terminating at its upper portion in a pair of protruding tabs which define spaced opposed slots so that an opposed end of the retainer will rest on the bottom of the vial in the interior of the elongated vial while permitting the retainer to be removed from the vial by gripping the upper portion of the retainer with medical or surgical instruments by use of the slots in the tabs.

The retainer is defined by a pair of elongated spaced oppositely-positioned members partially mediately joined along their length to define an opening in a lens retaining structure. A plurality of transversely extending retainer members or clips define relative to the joining wall a slotted space for receiving therein the haptic portion of an intraocular lens, and in particular a silicone or hydrogel intraocular lens. The inward extent of the retainer clips is limited so that the central portion of the lens retaining structure is axially and transversely open for receiving the optic portion of the lens, and for receiving an instrument for removing the lens from its retention in the slot structure.

Preferably, the material for the retainer is a Teflon brand material available from DuPont under the designation Type FEP100 which is particularly suitable for removably retaining a silicone lens. The Teflon is utilized to prevent the silicone from adhering to the surface of the retainer. Type FEP100 Teflon is utilized to match the FEP100 coated vial stopper for FDA acceptance. In use, the retainer is removed from the sterile liquid while continuing to retain the intraocular lens. The haptic of the lens may thus be used for lifting the lens away from the retainer by manipulating the haptic from beneath the clips on the retainer.

BRIEF DESCRIPTION OF THE DRAWINGS

In the drawings:

FIG. 1 is an exploded, highly-magnified, perspective view of the main components of the invention showing the retainer according to the invention, a lens, the mouth of a sterile vial, a cap member, and a stopper member for the vial, all of which are assembled to transport a retained lens in a sterile fashion;

FIG. 2 is a top view of the retainer inserted in the vial showing tabs and slots in the upper portion of the retainer;

DETAILED DESCRIPTION OF THE PREFERRED EMBODIMENTS

Figure 3:
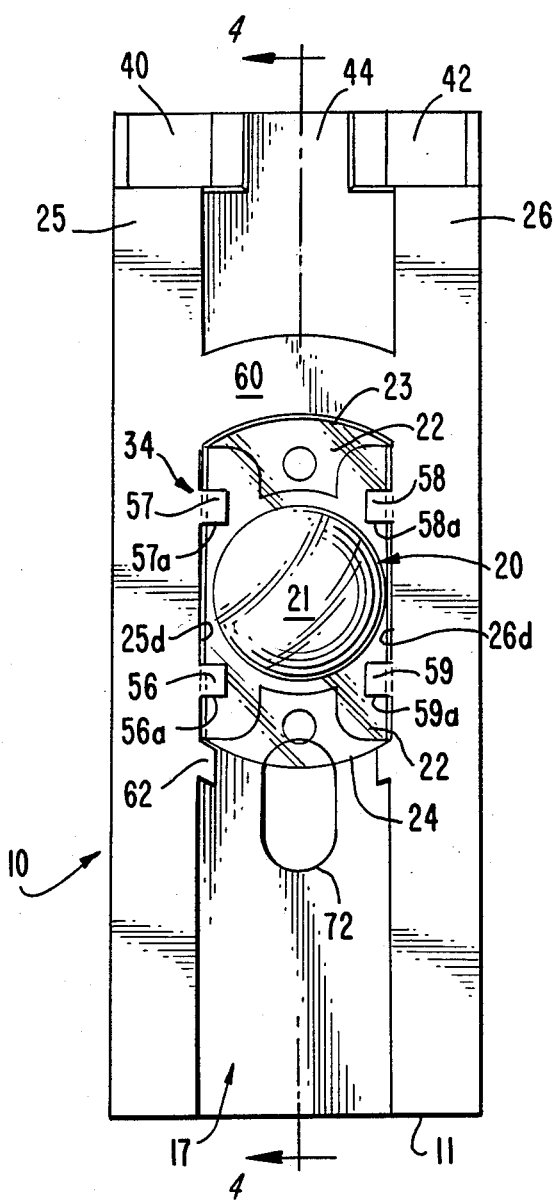
FIG. 3 is a top plan view of the retainer showing an intraocular lens retained thereon.

As shown in FIGS. 1-4, a retainer according to the invention is designated generally by the reference numeral 10. The retainer is generally elongated and structurally sized for easy insertion and removal into the interior of an elongated vial 12 (only the upper portion of which is shown) through an opening 13 constituting a mouth of the vial. When so positioned, the lower portion 11 of the retainer 10 rests on or near the bottom of the vial and slots in the upper portion lie in the neck portion 14 of the vial 12 in such a way that a stopper member 16 may be positioned thereon, over which an internally-threaded cap member 18 threadedly engages threads 19 in the upper neck portion of the vial. Vials of this description are known for this purpose, and a representative example is shown in U.S. Pat. No. 4,257,521, which is hereby incorporated by reference.

The retainer 10 is further structurally sized and adapted for receiving a lens designated generally by the reference numeral 20 of the type having a generally circular optic 21 and a haptic 22 to be received in slots therein, as will be further described.

Figure 4:
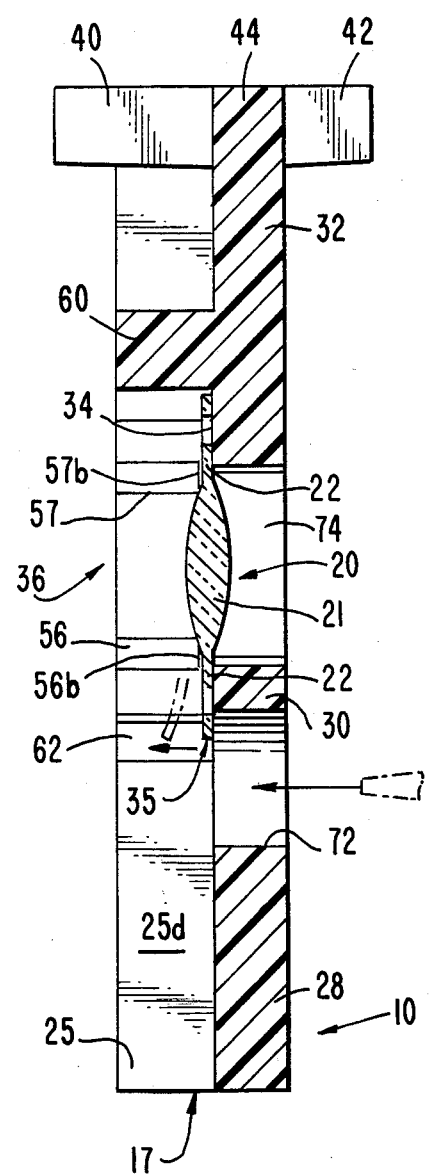
FIG. 4 is a cross-sectinal view of the retainer taken along line 4—4 of FIG. 3.

The optic 21 of a silicone intraocular lens is generally circular in a plan view and has curved surfaces extending above and below the upper and lower planes of the haptic 22, as best seen in FIG. 4. The haptic 22 has a thickness of about 0.25 mm, with generally planar upper and lower surfaces, terminating in fore and aft arcuate end surfaces 23 and 24, and is slightly resilient. The optic 21 ranges in thickness from 0.8 to 2.5 mm thick, while the lateral distance between the surfaces 23 and 24 is about 11 mm. The silicone posterior chamber lens 20 is available from Cooper Vision, Inc. under the trademark "NOVA Soft" and is made from a medical grade biocompatible silicone elastomer.

As best seen in FIGS. 3 and 4, the retainer 10 includes a pair of elongated wall portions 25, 26 spaced apart relative to an elongated axis of the retainer to define an opening 17 therebetween which is joined by intermediate wall portions 28, 30 and 32. The wall 28 has a thickness which is the same as the thickness of the wall portions 25, 26, 30, 32, as can been seen in FIG. 4, to define a lens retaining portion 34 in a lens retaining area 36. Thus, when viewed from its bottom, the retainer 10 has a generally U-shaped configuration.

As used in this specification, "lower" refers to the portion 11 of the retainer positioned at the base of the vial 12, while "upper" refers to the end of the retainer 10 nearer the mouth 13 of the vial 12.

The wall portions 25 and 26 terminate at their respective upward ends in a pair of spaced opposed tabs 40, 42. The spaced tabs 40, 42 are joined by a connecting wall portion 44 which merges into the wall portion 32 and is integral therewith, as can be seen in FIG. 4. The spaced opposed tabs 40, 42, together with wall portion 44 define a pair of spaced opposed slots 46, 48 which permit the retainer 10 to be removed from the mouth 13 of the vial by grasping the retainer in the slots 46, 48 by forceps, or other surgical instrument. The outer periphery of the tabs 40, 42 is shown by a connected plurality of line segments, but any convenient exterior shape is suitable for accommodation in the interior of the mouth 13 of the vial 12. Similarly, as can be seen in FIG. 1, the wall portion 26 is similarly configured by a plurality of surfaces 26a, 26b, and 26c, but the outer periphery of the retainer and its shape need only be sized and positioned to permit free entry and removal of the retainer 10 from the vial 12.

A plurality of retaining tabs 56, 57, 58 and 59 are formed on the interior surfaces 25d and 26d of the side walls 25, 26 as best seen in FIG. 3. The inward protrusion of each of the tabs 56-59 from the walls 25d and 26d toward the elongated internal areas of the retainer 10 is limited as defined by the length of the wall 56a, 57a, 58a and 59a. The lateral extent of the tab 56 is also limited to define between its lower portions 56b and 57b and the upper portion of the retaining walls 30, 32 a slotted space on the order of 0.017 inches to define a retaining area or slot 35, for the spaced opposed haptics 22 on the lens 20 as shown in FIG. 4. The lens 20 may be loaded in the retainer 10 by insertion therein from the lower end 11 and flexing the opposed generally parallel and linear edges of the haptics 22 slightly so that one side of the lens is positioned in the slot 35 beneath the tabs 56 and 57. The opposite side of the haptic can then be flexed inwardly slightly and positioned in the opening or slot 35 beneath the tabs 58 and 59 to be securely retained therein. It may be seen in FIG. 4 that such a structure defines an opening 36 for receiving the optic therein in an unencumbered spaced area.

Forward positioning of the intraocular lens 20 is limited by the arcuately-shaped wall 60 extending above the plane of the transitional members 28, 30, and 32 for a limited length, as best seen in FIG. 4. The lower portion of the wall 60 thus serves as a stop for the end 23 of the haptic 22 of the lens. Rearward travel of the lens 20 is similarly limited by the corresponding retaining wall 62, a major portion of which is removed to permit access to the lens through a slot 72.

The transitional walls 28 and 30 define the elongated slot 72 therein having an uppermost opening which is intended to overlie the lowermost surface 24 of the haptic 22 of the lens 20, as shown in FIGS. 3 and 4. Such an opening thus permits easy access from the lower side of the retainer for positioning and depositioning the lens from beneath the retainer ribs.

Removal of the lens 20 may be effected through the opening 74 beneath the optic portion of the lens or through the opening 72 so that an edge of the haptic may be grasped and slid from beneath the retainer ribs and directed upwardly so that the opposed haptic side will be removed from beneath the ribs on the other side.

The invention may be embodied in other specific forms without departing from its spirit or essential characteristics. The present embodiments are, therefore, to be considered in all respects as illustrative and not restrictive, the scope of the invention being indicated by the claims rather than by the foregoing description, and all changes which come within the meaning and range of the equivalents of the claims are therefore intended to be embraced therein.

What is claimed is:

1. A retainer for an intraocular lens having an optic and a haptic which is defined by a pair of elongated sides, said retainer being structurally adapted for retaining said lens on said retainer for insertion into a vial, said retainer comprising:

a pair of spaced, elongated side walls defining a lens receiving area between said side walls;

a transversely-extending wall portion connecting said side walls to define an interrupted supporting surface for supporting a haptic surface along each edge of said haptic, said interrupted supporting surface lying intermediate a thickness of said elongated sidewalls;

a plurality of ribs located on inner walls of said elongated side walls and extending inwardly toward an elongated axis of said retainer a limited predetermined distance, each of said ribs defining at an end surface thereof a slot formed by the end surface of said rib and a portion of said supporting surface of said transversely-extending wall portion, said slot having a dimension sized to receive the elongated edges of said haptic.

2. The retainer as set forth in claim 1 wherein said transversely-extending wall portion defines an opening in register with said lens receiving area so that the optic of said lens is free from contact with any portion of said retainer.

3. The retainer as set forth in claim 1 wherein said transversely-extending wall portion includes a stop wall located forward of said lens receiving area and connecting said elongated side walls, said stop wall portion located to inhibit forward lateral movement of said haptic when positioned in said slots.

4. The retainer as set forth in claim 3 further including a second stop means located rearward of said lens receiving area for inhibiting rearward movement of said haptic of said lens when positioned in said lens receiving area.

5. The retainer as set forth in claim 1 wherein said transversely-extending wall portion defines an access opening in register with an edge of said haptic when positioned in said slot to provide access to said lens by an instrument from a position remotely outside of said transversely-extending wall portion.

6. The retainer as set forth in claim 1 wherein said spaced, elongated side walls terminate in an end portion defining a pair of laterally extending tabs defining transversely spaced opposed slots therein, so that said retainer is centrally positioned in a vial, and its movement is restricted during shipping.

7. The retainer as set forth in claim 1 in combination with a vial having a neck portion sized to receive therein in an elongated position said retainer with a lens secured thereto, the upper portion of said retainer being sized and shaped to be accommodated within the neck portion of said vial.

8. The combination as set forth in claim 7 further including a cap member located adjacent the upper portion of said retainer and a stopper member secured to said vial.

9. The combination as set forth in claim 5 wherein said vial includes sterile fluid therein.

10. A retainer for a silicone intraocular lens having an optic and a haptic which is defined by a pair of elongated, generally parallel side walls having a predetermined thickness, said haptic further defining forward and trailing edges, said retainer comprising a body portion defining a slot structurally sized and shaped to retain said generally elongated side walls therein in a releasable relationship for ready removal from said retainer when said retainer has been removed from a vial, wherein said slot includes a lens receiving portion which is defined by a generally U-shaped cross-section, a leg of said U-shaped cross-section also defining said lens receiving portion; and ribs in said lens receiving portion terminating spacedly from a surface for receiving the elongated sides of said haptic so that said haptic may be flexed for insertion respectively in said slot defined between said ribs and said supporting surface to be retained therein in a predetermined location.

11. The retainer as set forth in claim 10 further including a wall portion spanning the opposed legs of said U-shaped cross-section and shaped to accommodate a leading edge of said haptic to inhibit forward movement of said haptic when said lens is retained in said lens receiving area.

12. The retainer as set forth in claim 11 wherein the transverse leg of said U-shaped cross-section defines an opening therein in register with a trailing edge of said haptic so that said lens may be accessed from a position exterior to said retainer.

13. A method for retaining an intraocular lens of the type having an optic and a haptic which is defined by a pair of elongated sides, said retainer being structurally adapted for retaining said lens on said retainer for insertion into and removal from a vial while attached thereto, said retainer being of the type comprising a pair of spaced, elongated side walls defining a slotted, lens-receiving area between said side walls; a transversely-extending wall portion connecting said side walls to define an interrupted supporting surface for supporting a haptic surface along each edge of said haptic; and a plurality of ribs located on inner walls of said elongated walls and extending inwardly toward an elongated axis of said retainer a predetermined distance, each of said ribs defining at an end surface thereof a slot formed by the end surface of said rib and a portion of said supporting surface, said slot having a dimension sized to receive an elongated edge of said haptic, the method including the steps of:

providing an intraocular lens of the type described;
positioning said lens in said lens-receiving area;
inserting an edge of said haptic in said slot on one side of said pair of elongated side walls; and
flexing said lens until the opposed edges of said haptic are inserted into an opposed slot.

14. The method as set forth in claim 13 further including the step of removing said lens from said retainer, comprising:

accessing said lens while retained in the lens receiving area of said retainer by an instrument through an access opening defined in said transversely-extending wall portion to slideably remove said lens from said slot.

* * * * *